United States Patent
Zink et al.

(10) Patent No.: US 11,321,826 B2
(45) Date of Patent: May 3, 2022

(54) HIGH THROUGHPUT METHOD FOR ACCURATE PREDICTION OF COMPOUND-INDUCED LIVER INJURY

(71) Applicant: AGENCY FOR SCIENCE, TECHNOLOGY AND RESEARCH, Singapore (SG)

(72) Inventors: Daniele Zink, Singapore (SG); Nur Faezah Begum Akbar Hussain, Singapore (SG); Lit Hsin Loo, Singapore (SG); Ah Wah Lam, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 868 days.

(21) Appl. No.: 16/093,139

(22) PCT Filed: Apr. 11, 2017

(86) PCT No.: PCT/SG2017/050206
§ 371 (c)(1),
(2) Date: Oct. 11, 2018

(87) PCT Pub. No.: WO2017/180061
PCT Pub. Date: Oct. 19, 2017

(65) Prior Publication Data
US 2021/0183053 A1      Jun. 17, 2021

(30) Foreign Application Priority Data
Apr. 11, 2016  (SG) .............................. 10201602855P

(51) Int. Cl.
*G06K 9/00*       (2022.01)
*G06T 7/00*       (2017.01)
(Continued)

(52) U.S. Cl.
CPC ....... *G06T 7/0012* (2013.01); *G01N 33/5008* (2013.01); *G01N 33/533* (2013.01);
(Continued)

(58) Field of Classification Search
CPC ......... G06T 7/0012; G06T 2207/10064; G06T 2207/20081; G06T 2207/30024;
(Continued)

(56) References Cited

U.S. PATENT DOCUMENTS

| 2003/0048931 A1* | 3/2003 | Johnson ................ G06T 7/0012 |
| | | 382/128 |
| 2005/0014217 A1* | 1/2005 | Mattheakis ........ G01N 33/5067 |
| | | 435/40.5 |

(Continued)

FOREIGN PATENT DOCUMENTS

| WO | 20090002565 A1 | 12/2008 |
| WO | WO-2009002565 A1 * | 12/2008 ......... G01N 33/5067 |

OTHER PUBLICATIONS

Tolosa, Laia, et al. "Development of a multiparametric cell-based protocol to screen and classify the hepatotoxicity potential of drugs." Toxicological Sciences 127.1 (2012): 187-198. (Year: 2012).*

(Continued)

*Primary Examiner* — Avinash Yentrapati
(74) *Attorney, Agent, or Firm* — Womble Bond Dickinson (US) LLP

(57) ABSTRACT

A method and system for predicting liver injury in vivo due to hepatocyte damage by a test compound are provided. The method includes acquiring images of fluorescently stained cells obtained from a cell culture in which the cells have been treated with a dose-range of at least the test compound and its vehicle. The cells may be hepatic cells including primary or immortalized hepatocytes, hepatoma cells or induced pluripotent stem cell-derived hepatocyte-like cells.

(Continued)

The acquired images are segmented. The method further includes extracting and analyzing one or more phenotypic features from the segmented images, wherein the one or more phenotypic features are selected from the group of intensity, textural, morphological, or ratiometric features consisting of (a) features of DNA, (b) features of RELA (NF-KB p65), and (c) features of actin filaments at different subcellular regions and d) features of cellular organelles and their substructures in the segmented images. Finally, the method includes normalizing results from the treated samples to vehicle controls and predicting the probability of liver injury by the test compound based on test compound-induced normalized changes of the extracted and selected phenotypic features using machine learning methods.

20 Claims, 9 Drawing Sheets

(51) Int. Cl.
  *G16H 50/20* (2018.01)
  *G16H 30/40* (2018.01)
  *G16B 20/00* (2019.01)
  *G01N 33/50* (2006.01)
  *G01N 33/533* (2006.01)

(52) U.S. Cl.
  CPC ............. *G16B 20/00* (2019.02); *G16H 30/40* (2018.01); *G16H 50/20* (2018.01); *G06T 2207/10064* (2013.01); *G06T 2207/20081* (2013.01); *G06T 2207/30024* (2013.01); *G06T 2207/30056* (2013.01)

(58) Field of Classification Search
  CPC .......... G06T 2207/30056; G16H 50/20; G16H 30/40; G16B 20/00; G01N 33/5008; G01N 33/533
  See application file for complete search history.

(56) References Cited

U.S. PATENT DOCUMENTS

| | | | | |
|---|---|---|---|---|
| 2005/0262031 | A1* | 11/2005 | Saidi | G16Z 99/00 600/407 |
| 2008/0281526 | A1* | 11/2008 | Diggans | G16B 25/00 702/19 |
| 2010/0177950 | A1* | 7/2010 | Donovan | G16H 50/50 702/19 |
| 2010/0184093 | A1* | 7/2010 | Donovan | G16H 50/50 435/287.1 |
| 2012/0010528 | A1* | 1/2012 | Donovan | G06V 20/698 382/128 |
| 2012/0219204 | A1* | 8/2012 | Hong | G01N 33/5067 382/133 |
| 2013/0080134 | A1* | 3/2013 | Donovan | G16Z 99/00 703/11 |
| 2013/0208969 | A1* | 8/2013 | Bashir | G06T 7/0012 382/131 |
| 2016/0042514 | A1* | 2/2016 | Amat Roldan | A61B 8/0891 382/131 |

OTHER PUBLICATIONS

Su, Ran, et al. "High-throughput imaging-based nephrotoxicity prediction for xenobiotics with diverse chemical structures." Archives of toxicology 90.11 (2016): 2793-2808. (Year: 2016).*
Foitzik, Angelika; et al.; "Application Note: Cytotoxicity Studies on Live Primary Human Hepatocytes Using Operetta"; Perkin Elmer, Inc.; May 2011; 4 pp.
Kikkoman; "Kikkoman Ends Animal Tests"; PETA; 2 pp. http://www.peta.org/action/action-alerts/kikkoman-ends-animal-tests/.
Kretzer, Michelle; "Countries Around the World Work to Ban Cosmetics Testing on Animals"; Peta; dated Jul. 21, 2015; 3 pp http://www.peta.org/blog/countries-around-the-world-work-to-ban-cosmetics-testing-on-animals/.
Loo, L.-H., et al.; "Image-based multivariate profiling of drug responses from single cells". Nature Methods, Apr. 1, 2007, vol. 4, No. 5, pp. 445-453; 10 pp.
Mennecozzi M., et al., "Hepatotoxicity Screening Taking a Mode-Of-Action Approach Using HepaRG Cells and HCA". ALTEX-Proceedings, Jan. 2012, vol. 1, No. 1, pp. 193-204; 12 pp.
Peta; "Coca Cola Stops Animal Tests"; Peta; dated Oct. 19, 2017; 2 pp. http://www.peta.org/blog/cocacola-stops-animal-tests/.
Sirenko, Oksana, et al.; "High-Content Assays for Hepatotoxicity Using Induced Pluripotent Stem Cell-Derived Cells". Assay Drug Dev Technologies; dated Jan./Feb. 2014 vol. 12, No. 1, pp. 43-54; 12 pp.
Su, R.; et al., "High-Throughput Imaging-Based Nephrotoxicity Prediction for Xenobiotics with Diverse Chemical Structures". Arch Toxicol, Nov. 27, 2015, vol. 90, No. 11, pp. 2793-2808; 16 pp.
Tencza, Sarah B., et al.; "Detection and Classification of Threat Agents via High-Content Assays of Mammalian Cells". J Applied Toxicology, Sep. 2004, vol. 24, No. 5, pp. 371-377; 16 pp.
Tolosa L., et al.; "Development of a Multiparametric Cell-based Protocol to Screen and Classify the Hepatotoxicity Potential of Drugs". Toxicol Sciences, Feb. 13, 2012, vol. 127, No. 1, pp. 187-198; 12 pp.
Ward-Sherry L., et al.; "Table of Validated and Accepted Alternative Methods"; AltTox.org; Nov. 20, 2016; 20 pp. http://alttox.org/mapp/table-of-validated-and-accepted-alternative-methods/.
Xu J.J., et al. "Cellular Imaging Predictions of Clinical Drug-Induced Liver Injury". Toxicol Science, Jun. 3, 2008, vol. 105, No. 1, pp. 97-105.
PCT Notification Transmittal of the "International Search Report" of Counterpart International PCT Application No. PCT/SG2017/050206; dated Aug. 10, 2017; 5 pp.
PCT Notification Transmittal of the "Written Opinion" of Counterpart International PCT Application No. PCT/SG2017/050206; dated Aug. 10, 2017; 7 pp.
PCT Notification Transmittal of the "International Preliminary Report on Patentability" of Counterpart International PCT Application No. PCT/SG2017/050206; dated Aug. 10, 2017; 5 pp.

* cited by examiner

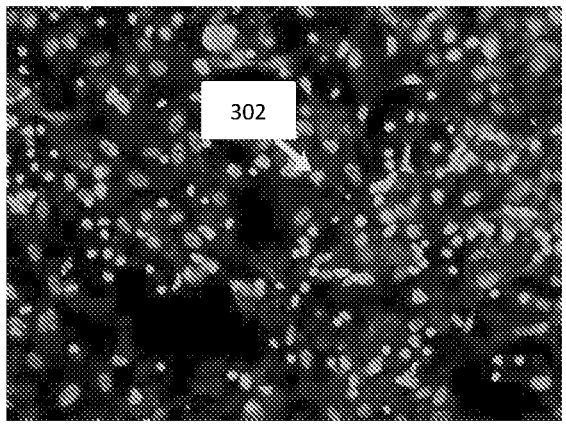
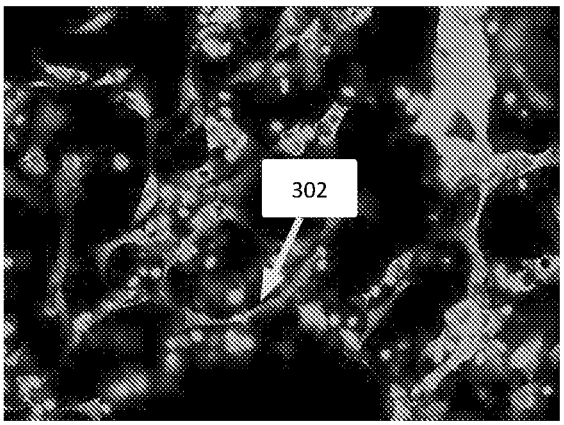
300  *FIG. 3A*          *FIG. 3B*  310
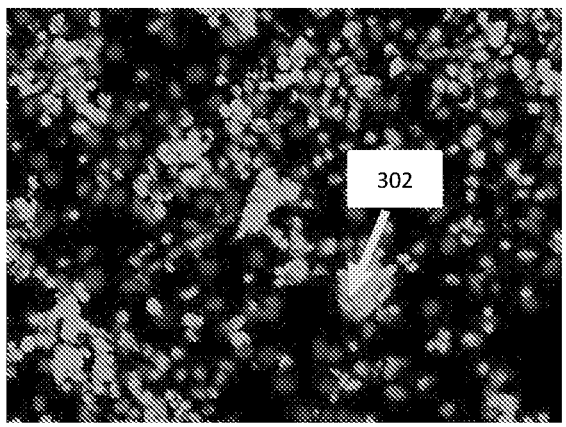
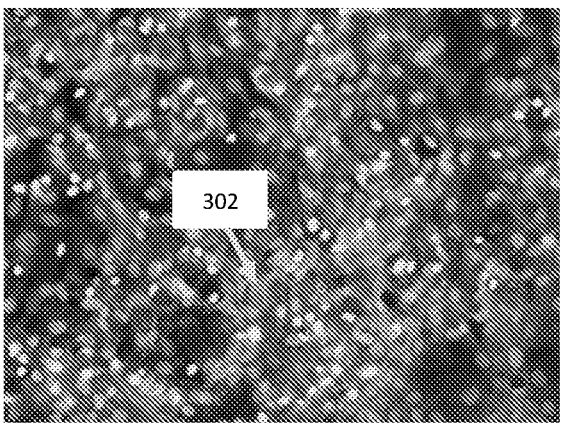
320  *FIG. 3C*          *FIG. 3D*  330
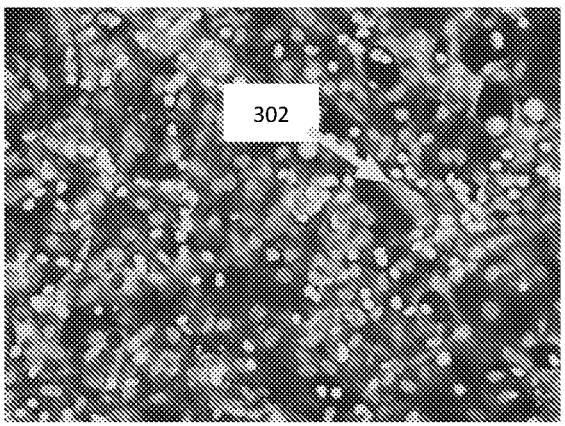
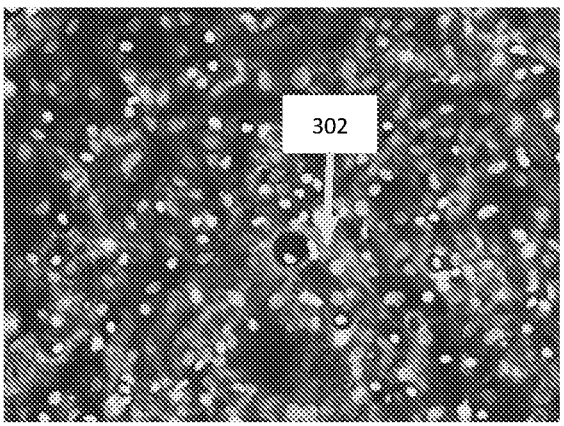
340  *FIG. 3E*          *FIG. 3F*  350

| S/N | Chemicals | Hepatocyte Toxicity *In Vivo* |
|---|---|---|
| 1 | Acarbose | + |
| 2 | Acesulfame potassium | - |
| 3 | Acetamidophenol | - |
| 4 | Acetaminophen | - |
| 5 | Allantoin | - |
| 6 | Aristolochic acid | + |
| 7 | Arsenic(III) oxide | + |
| 8 | Artemisinin | - |
| 9 | Ascorbate | - |
| 10 | Aspartame | - |
| 11 | Azathioprine | + |
| 12 | Azithromycin | + |
| 13 | Betaine | - |
| 14 | Bicalutamide | + |
| 15 | Bismuth(III) oxide | + |
| 16 | Cadmium(II) chloride | + |
| 17 | Caffeine | - |
| 18 | Capecitabine | - |
| 19 | Cephaloridine | - |
| 20 | Chloral hydrate | - |
| 21 | Cinchophen | + |
| 22 | Ciprofloxacin | + |
| 23 | Cisplatin | - |
| 24 | Citrinin | - |
| 25 | Clofibrate | - |
| 26 | Colestipol | - |
| 27 | Copper(II) chloride | + |
| 28 | Cyclosporin A | + |
| 29 | Cyproterone acetate | + |
| 30 | D-alpha-Tocopherol | - |
| 31 | Dacarbazine | + |
| 32 | Diclofenac | + |
| 33 | Diltiazem HCl | + |
| 34 | DOPA | - |
| 35 | Dutasteride | - |
| 36 | Emtricitabine | - |
| 37 | Epigallocatechin gallate | + |
| 38 | Eplerenone | - |
| 39 | Ethylene glycol | - |
| 40 | Felbamate | + |
| 41 | Finasteride | - |
| 42 | 5-Flurouracil | + |

*FIG. 4*

| 43 | Flutamide | + |
|---|---|---|
| 44 | Furosemide | + |
| 45 | Garcinia acid | - |
| 46 | Gentamycin sulfate | - |
| 47 | Glutathione | - |
| 48 | Glycine | - |
| 49 | Gold(I) chloride | + |
| 50 | Halothane | + |
| 51 | Ibuprofen | + |
| 52 | Ifosfamide | - |
| 53 | Isoniazid | + |
| 54 | Ketoconazole | + |
| 55 | Ketorolac | - |
| 56 | Leflunomide | + |
| 57 | Lincomycin | - |
| 58 | Lithium chloride | - |
| 59 | Melatonin | - |
| 60 | Menthol | - |
| 61 | Metformin HCl | - |
| 62 | Methotrexate | + |
| 63 | Methyl vanillate | - |
| 64 | Modafinil | - |
| 65 | N-acetyl-cysteine | - |
| 66 | Naloxone | - |
| 67 | Naltrexone HCl | - |
| 68 | Naproxen | + |
| 69 | Nevirapine | + |
| 70 | Nicotine | - |
| 71 | Penicillin | - |
| 72 | Phenacetin | - |
| 73 | Potassium dichromate | + |
| 74 | Probenecid | - |
| 75 | Promethazine | - |
| 76 | Ranitidine HCl | + |
| 77 | Retinoic acid | - |
| 78 | Ribavirin | - |
| 79 | Rifampicin | + |
| 80 | Simvastatin | - |
| 81 | Sodium chloride | - |
| 82 | Sodium valproate | + |
| 83 | Stavudine (d4T) | + |
| 84 | Sucrose | - |
| 85 | Sunitinib malate | + |
| 86 | Tacrolimus | - |
| 87 | Tetracycline | + |
| 88 | Theophylline | - |

*FIG. 4 (continued)*

| 89 | Tigecycline | - |
|---|---|---|
| 90 | Tolcapone | + |
| 91 | Tolvaptan | + |
| 92 | Torsemide | - |
| 93 | Triptolide | + |
| 94 | Trisodium citrate dihydrate | - |
| 95 | Troglitazone | + |
| 96 | Valacyclovir | - |
| 97 | Vancomycin | + |
| 98 | Vardenafil HCl | - |

*FIG. 4 (continued)*

| No. | Feature set | $\Delta_{max}$ concentration | Test Sensitivity | Test specificity | Test accuracy |
|---|---|---|---|---|---|
| 1 | Coefficient of variation of DNA intensity at the chromosomal region | 1mM | 61.4% | 86.1% | 73.8% |
| 2 | Average of the sum average of DNA GLCM at the nuclear region | 1mM | 56.0% | 89.5% | 72.7% |
| 3 | Average intensity of RELA at the chromosomal region | 1mM | 53.1% | 89.6% | 71.4% |
| 4 | Fraction of the total intensity of RELA objects at the nuclear region | 1mM | 47.9% | 92.1% | 70.0% |

*FIG. 5*

| S/N | Chemicals | Hepatocyte Toxicity *In Vivo* |
|---|---|---|
| 1 | Acesulfame Potassium | - |
| 2 | Arsenic (III) Oxide | + |
| 3 | Aspartame | - |
| 4 | Azathioprine | + |
| 5 | Cadmium (II) Chloride | + |
| 6 | Caffeine | - |
| 7 | Chloral Hydrate | - |
| 8 | Citrinin | - |
| 9 | Clofibrate | - |
| 10 | Cyclosporin A | + |
| 11 | Diclofenac | + |
| 12 | Felbamate | + |
| 13 | 5-Flurouracil | + |
| 14 | Garcinia Acid | - |
| 15 | Glutathione | - |
| 16 | Glycine | - |
| 17 | Gold (I) Chloride | + |
| 18 | Isoniazid | + |
| 19 | Modafinil | - |
| 20 | Nicotine | - |
| 21 | Ranitidine HCl | + |
| 22 | Tetracycline | + |
| 23 | Torsemide | - |
| 24 | Vancomycin | + |

*FIG. 6*

HIGH THROUGHPUT METHOD FOR ACCURATE PREDICTION OF COMPOUND-INDUCED LIVER INJURY

CROSS-REFERENCE TO RELATED APPLICATIONS

This patent application is a U.S. National Phase Application under 35 U.S.C. § 371 of International Application No. PCT/SG2017/050206, filed on 11 Apr. 2017, entitled HIGH THROUGHPUT METHOD FOR ACCURATE PREDICTION OF COMPOUND-INDUCED LIVER INJURY, which claims priority from Singapore Patent Application No. 10201602855P filed on 11 Apr. 2016.

PRIORITY CLAIM

The present application claims priority from Singapore Patent Application No. 10201602855P filed 11 Apr. 2016.

TECHNICAL FIELD

The present invention generally relates to compound-induced hepatotoxicity, and more particularly relates to a high-throughput method and system for accurate prediction of compound-induced liver injury based on hepatocyte damage in vivo.

BACKGROUND OF THE DISCLOSURE

The liver is the main human target organ for compound-induced toxicity. Compounds that damage the liver include drugs, herbal and fungal compounds, food and cosmetics ingredients, dietary supplements, industrial chemicals and environmental toxicants. Thus, compound-induced hepatotoxicity must be addressed by the chemical, food and nutrition, cosmetics and consumer care and pharmaceutical industries.

Drug-induced liver injury is a leading cause for acute liver failure requiring organ transplantation. Regulatory animal toxicity studies with combined rodent and non-rodent species identify only about fifty percent of compounds that are hepatotoxic in humans. The low sensitivity of current preclinical hepatotoxicity models is one of the major reasons for attrition during late stages of development and is also the reason why drugs continue to be pulled from the market because of previously undetected hepatotoxicity.

Improved platforms for the prediction of hepatotoxicity are also required by the cosmetics industry, where there is a particular need for animal-free predictive platforms. Animal models cannot be used anymore for the testing of cosmetics developed or marketed in Europe, Norway, Israel and India due to animal testing bans. New Zealand, Canada, Taiwan, Brazil, Korea and also probably Argentina, USA and China are expected to follow.

Also, the food industry is now under substantial pressure from animal activist groups. Under this pressure, large food companies like Coca Cola have stopped using animal testing, the last food company having given into this pressure being Kikkoman. Accordingly, animal-free platforms for the accurate prediction of hepatotoxicity and other toxicities in humans are urgently required. Accepted in vitro or in silico models do not exist with respect to liver, kidney and other organs.

Thus, what is needed is methods and systems for high throughput in vitro modelling of compound-induced liver injury which provides accurate prediction of such compound-induced liver injury. Methods and systems based on high-throughput screening that are highly scalable and suitable for testing of large compound libraries at an industrial scale is also needed. Furthermore, other desirable features and characteristics will become apparent from the subsequent detailed description and the appended claims, taken in conjunction with the accompanying drawings and this background of the disclosure.

SUMMARY

In one aspect, there is provided a method for predicting liver injury induced by a test compound comprising: acquiring images of fluorescently stained cells obtained from a cell culture in which the cells have been treated with a dose-range of at least the test compound and its vehicle; segmenting the acquired images; extracting and analyzing one or more phenotypic features from the segmented images, wherein the one or more phenotypic features are selected from the group of intensity, textural, morphological, or ratiometric features consisting of (a) features of DNA, (b) features of a RELA (NF-□B p65), (c) features of actin filaments at different subcellular regions and d) features of cellular organelles and their substructures in the segmented images; normalizing results from the treated samples to vehicle controls; and predicting a probability of liver injury by the test compound based on test compound-induced normalized changes of the extracted and selected phenotypic features using machine learning methods.

In an embodiment, extracting and selecting the one or more phenotypic features from the segmented images may comprise extracting and selecting the coefficient of variation of the intensity of a DNA marker at chromosomal regions in the segmented images.

In an embodiment, extracting and selecting the one or more phenotypic features from the segmented images may comprise extracting and selecting an average of a sum average of the intensity of a DNA marker determined from a grey-level co-occurrence matrix (GLCM) at nuclear regions in the segmented images.

In an embodiment, extracting and selecting the one or more phenotypic features from the segmented images may comprise extracting and selecting an average of the intensity of a RELA marker at chromosomal regions in the segmented images.

In an embodiment, extracting and selecting the one or more phenotypic features from the segmented images may comprise extracting and selecting a fraction of the intensity of objects based on a RELA marker at nuclear regions in the segmented images.

In an embodiment, the cells may be selected from the group comprising hepatic cells, induced pluripotent stem cell (iPS)-derived hepatocyte-like cells, primary hepatocytes, an (immortalized) hepatocyte cell line, and hepatoma cells.

In an embodiment, the hepatic cells may be derived from hepatic progenitor-like cells.

In an embodiment, the cells are human cells. In another embodiment, the cells are animal cells.

In an embodiment, the hepatic cells may be HepaRG™ cells.

In an embodiment, the cells of the cell culture may be cultured in a 2D culture.

In an embodiment, the may further comprising the step of fluorescently labelling the cells for detection of one or more of DNA, RELA (NF-κB p65), F-actin, gammaH2AX and the whole cells.

In an embodiment, treating the cells may comprise treating with the at least one test compound and the vehicle for a predetermined time duration of at least twelve hours or overnight.

In an embodiment, treating the cells may comprise treating with the at least one test compound and the vehicle for a predetermined time duration of sixteen hours or greater.

In an embodiment, predicting hepatotoxicity may comprise: treating the cells with a dose-range of at least one test compound and the vehicle; determining maximal response values ($\Delta_{max}$) with respect to the phenotypic features; and using machine learning methods to predict hepatotoxicity based on the compound-induced feature changes.

In an embodiment, using machine learning methods to predict hepatotoxicity may comprise using machine learning methods that use a median of the maximal response values ($\Delta_{max}$) of the selected and normalized phenotypic feature changes of the cells for compound classification.

In an embodiment, the maximal response values may comprise response values at a concentration of 1 mM, 2 mM or 5 mM of the test compound.

In an embodiment, predicting liver toxicity may comprises: normalizing the phenotypic features from different test compounds to a same range when more than one test compound is tested; and predicting liver toxicity by using a machine learning classification algorithm that has been trained with a training set of compounds that is statistically independent from a test set of compounds.

In an embodiment, the machine learning classification algorithm may be a random-forest algorithm or a support vector machine.

In another aspect, there is provided a system for predicting liver injury induced by at least one test compound comprising: an apparatus for treating a cell culture with the at least one test compound and its vehicle and staining the cell culture for fluorescent detection; an imaging device arranged with respect to the apparatus to acquire images of the fluorescently stained cells for detecting the cells and their stained components; and a computing device coupled to the imaging device for receiving and segmenting the acquired images, the computing device comprising a feature extraction module for extracting and analyzing one or more phenotypic features from the segmented images, wherein the one or more phenotypic features are selected from the group of intensity, textural, morphological, or ratiometric features consisting of (a) features of DNA, (b) features of a RELA (NF-☐B p65), and (c) features of actin filaments at different subcellular regions and d) features of cellular organelles and their substructures in the segmented images, the computing device further comprising a prediction module for normalizing results from the treated samples to vehicle controls and predicting a probability of liver injury by the test compound based on test compound-induced normalized changes of the extracted and selected phenotypic features using machine learning methods.

In an embodiment, the feature extraction module may extract and select a phenotypic feature from the segmented images measuring a coefficient of variation of the intensity of a DNA marker at chromosomal regions in the segmented images.

In an embodiment, the feature extraction module may extract and select a phenotypic feature from the segmented images measuring an average of a sum average of the intensity of a DNA marker determined from a grey-level co-occurrence matrix (GLCM) at nuclear regions in the segmented images.

In an embodiment, the feature extraction module may extract and select a phenotypic feature from the segmented images measuring an average of the intensity of a RELA marker at chromosomal regions in the segmented images.

In an embodiment, the feature extraction module may extract and select a phenotypic feature from the segmented images measuring a fraction of the intensity of objects based on a RELA marker at nuclear regions in the segmented images.

In an embodiment, the prediction module of the computing device may predict hepatotoxicity by using machine learning methods based on maximum response values ($\Delta_{max}$) with respect to the phenotypic feature changes of the cells treated with the at least one test compound and the vehicle.

In an embodiment, the prediction module of the computing device may predict hepatotoxicity by using machine learning methods that uses a median of the maximum response values ($\Delta_{max}$) of the selected and normalized phenotypic feature changes.

In an embodiment, the maximum response values may comprise response values at a compound concentration of 1 mM, 2 mM or 5 Mm of the test compound.

In an embodiment, the prediction module of the computing device may predict hepatotoxicity based on changes of phenotypic features normalized to a same range when more than one test compound is used and by using a machine learning classification algorithm trained with a statistically independent training set of compounds.

In an embodiment, the machine learning classification algorithm may be a random forest algorithm or a support vector machine.

According to at least one embodiment of the present invention, a method for predicting liver injury in vivo due to hepatocyte damage by a test compound is provided. The method includes acquiring images of fluorescently stained cells obtained from a cell culture in which the cells have been treated with a dose-range of at least the test compound and its vehicle and segmenting the acquired images. The method further includes extracting and analyzing one or more phenotypic features from the segmented images, wherein the one or more phenotypic features are selected from the group of intensity, textural, morphological, or ratiometric features consisting of (a) features of DNA, (b) features of a RELA (NF-κB p65), (c) features of actin filaments at different subcellular regions, and (d) features of cellular organelles and their substructures in the segmented images. Finally, the method includes normalizing results from the treated samples to vehicle controls and predicting a probability of liver injury by the test compound based on test compound-induced normalized changes of the extracted phenotypic features using a machine learning methods.

According to another embodiment of the present invention, a system for predicting liver injury in vivo due to hepatocyte damage by at least one test compound is provided. The system includes an apparatus for treating a cell culture with the at least one test compound and its vehicle and staining the cells for fluorescent detection, an imaging device and a computing device. The imaging device is arranged with respect to the apparatus to acquire images of the fluorescently stained cells for detecting the cells and their stained components. The computing device is coupled to the imaging device for receiving and segmenting the acquired images. The computing device includes a feature extraction module for extracting and analyzing one or more phenotypic features from the segmented images, wherein the one or more phenotypic features are selected from the group of intensity, textural, morphological, or ratiometric features consisting of (a) features of DNA, (b) features of a RELA (NF-κB p65), (c) features of actin filaments at different subcellular regions, and (d) features of cellular organelles and their substructures in the segmented images. The computing device also includes a prediction module for normalizing results from the treated samples to vehicle controls and predicting a probability of liver injury by the test compound based on test compound-induced normalized changes of the extracted phenotypic features using machine learning methods.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 3, comprising FIGS. 3A to 3F, depicts exemplary immunofluorescence image data obtained with different compounds by nuclear and NF-κB staining in accordance with the present embodiment.

FIG. 4 depicts a table of reference compound information used for validation of the high-throughput method with HepaRG cells in accordance with the present embodiment for accurate prediction of compound-induced injury.

FIG. 5 depicts a table of phenotypic feature sets and their prediction performances with HepaRG cells in accordance with the present embodiment.

FIG. 6 depicts a table of reference compound information used for pre-validation of the high-throughput method with induced pluripotent stem cell (iPS)-derived hepatocyte-like cells in accordance with the present embodiment for accurate prediction of compound-induced injury.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. In the following description, the liver is the liver of an animal, such as non-human mammal and human, including, without limitation, animals classed as bovine, porcine, equine, canine, lupine, feline, murine, ovine, avian, piscine, caprine, corvine, acrine, or delphine. In one example, the liver is a human liver. It is the intent of the present embodiment to present a high-throughput system and method for the accurate prediction of hepatocyte toxicity in vivo that combines automated imaging of hepatocytes with automated computational analysis of the image data by phenotypic profiling results classification utilizing machine learning.

Unlike conventional systems and methods which determine the toxicity of compounds for cultivated hepatocytes, systems and methods in accordance with the present embodiment examine changes induced in in vitro cultivated cells and use those observed changes to predict hepatocyte toxicity in vivo.

Optimal results are obtained with HepaRG™ cells, which is one of the most promising hepatocyte models. The HepaRG™ cell line is a human bipotent progenitor cell line capable to differentiate toward two different cell phenotypes (i.e., biliary-like and hepatocyte-like cells). This cell line has been established from a liver tumor associated with chronic hepatitis C. HepaRG cells exhibit many characteristics of primary human hepatocytes, including morphology and expression of key metabolic enzymes, nuclear receptors, and drug transporters. Unlike HepG2 and Fa2N-4 cells, HepaRG cells have high P450 activity and complete expression of all nuclear receptors. iPS-derived human hepatocyte-like cells, primary human hepatocytes and other human hepatocyte cell lines may also be suitable.

Figure 1:
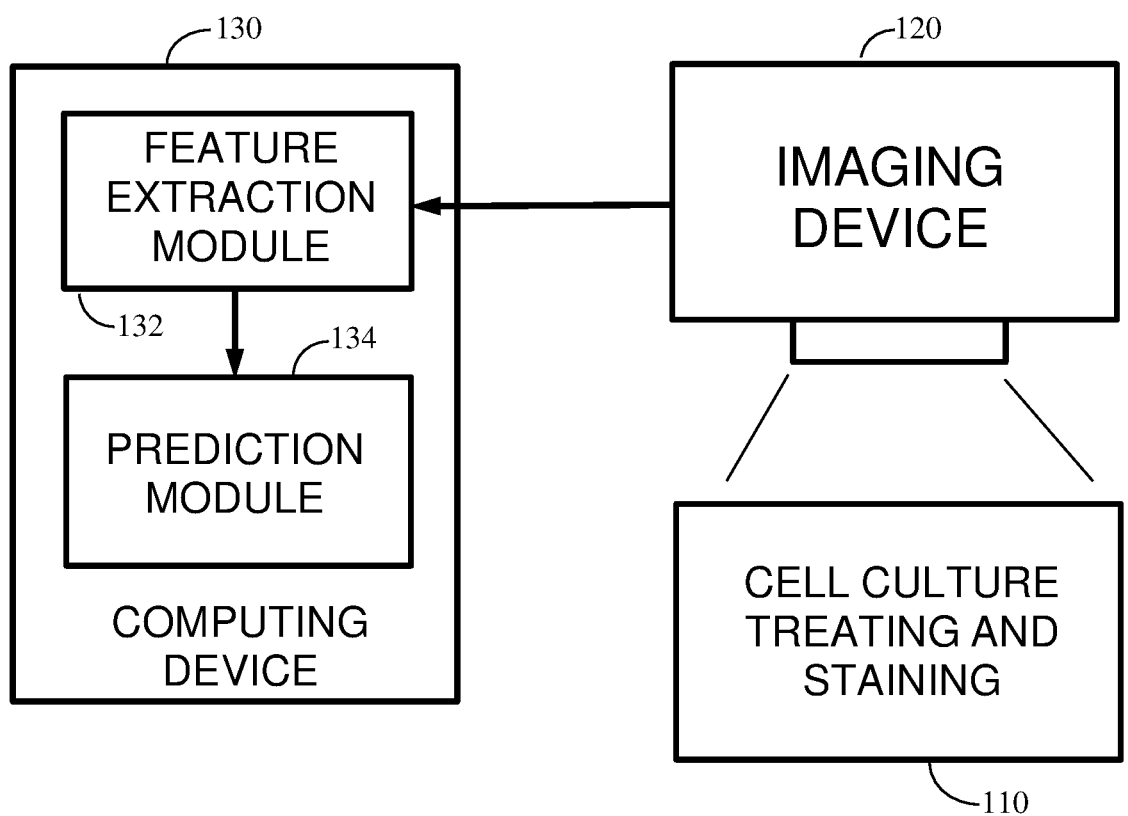
FIG. 1 depicts a block diagram of a system for predicting liver injury in accordance with a present embodiment, the liver injury induced by at least one test compound.

Referring to FIG. 1, a block diagram 100 depicts a system for the prediction of liver injury in accordance with a present embodiment. The system 100 includes a cell culture and staining apparatus 110. Within the cell culture and staining apparatus 110, a cell culture is treated with the test compounds and a vehicle for compound exposure for a period of sixteen or more hours. After compound treatment, the treated cells are stained for fluorescent detection and various cellular components (DNA, RELA (NF-KB p65) and F-actin) and the whole cells are thereby fluorescently labeled. Thus, in accordance with the present embodiment, human hepatocytes are cultivated as two-dimensional (2D) monolayers in collagen-coated standard multi-well plates of the cell culture and staining apparatus 110. While currently HepaRG cells are used, primary human hepatocytes, iPS-derived hepatocyte-like cells and other types of hepatocytes or hepatocyte-like cells may be suitable in accordance with the present embodiment.

An imaging device 120 is optically arranged with respect to the cell culture and staining apparatus 110 to acquire images of the fluorescently stained cells for detecting the cells and their stained components. The imaging device 120 is a high content analyzer which automatically images the fluorescently stained cells to obtain immunofluorescent detection of RELA (NF-kB p65), F-actin, gammaH2AX and 4',6-diamidino-2-phenylindole (DAPI, DNA detection)) and whole cell stain (WCS) detection after the compound treatment.

The imaging device 120 provides the acquired images to a computing device 130 which is coupled to the imaging device 120 to receive and segment the acquired images. The computing device 130 analyzes phenotypic features by phenotypic profiling and uses machine learning methods for results classification and predictive performance analysis.

The computing device 130 includes a feature extraction module 132 which extracts one or more phenotypic features from the segmented images. In accordance with the present embodiment, a phenotypic feature is extracted by the feature extraction module 132 which is selected from the group of phenotypic features including (a) intensity or texture features of DNA marker at chromosomal or nuclear regions in the segmented images, and (b) intensity or ratiometric features of a RELA marker at chromosomal or nuclear regions in the segmented images. The computing device 130 also includes a prediction module 134 coupled to the feature extraction module 132 which uses the extracted phenotypic features to predict liver injury. More particularly, in accordance with the present embodiment, the prediction module 134 predicts hepatocyte toxicity in vivo using a supervised classifier developed using the phenotypic features. The system of the present embodiment advantageously provides high predictivity with a test sensitivity of 61.4%, a test specificity of 86.1% and a test balanced accuracy of 73.8%, a result significantly improved over conventional methods and systems.

Figure 2:
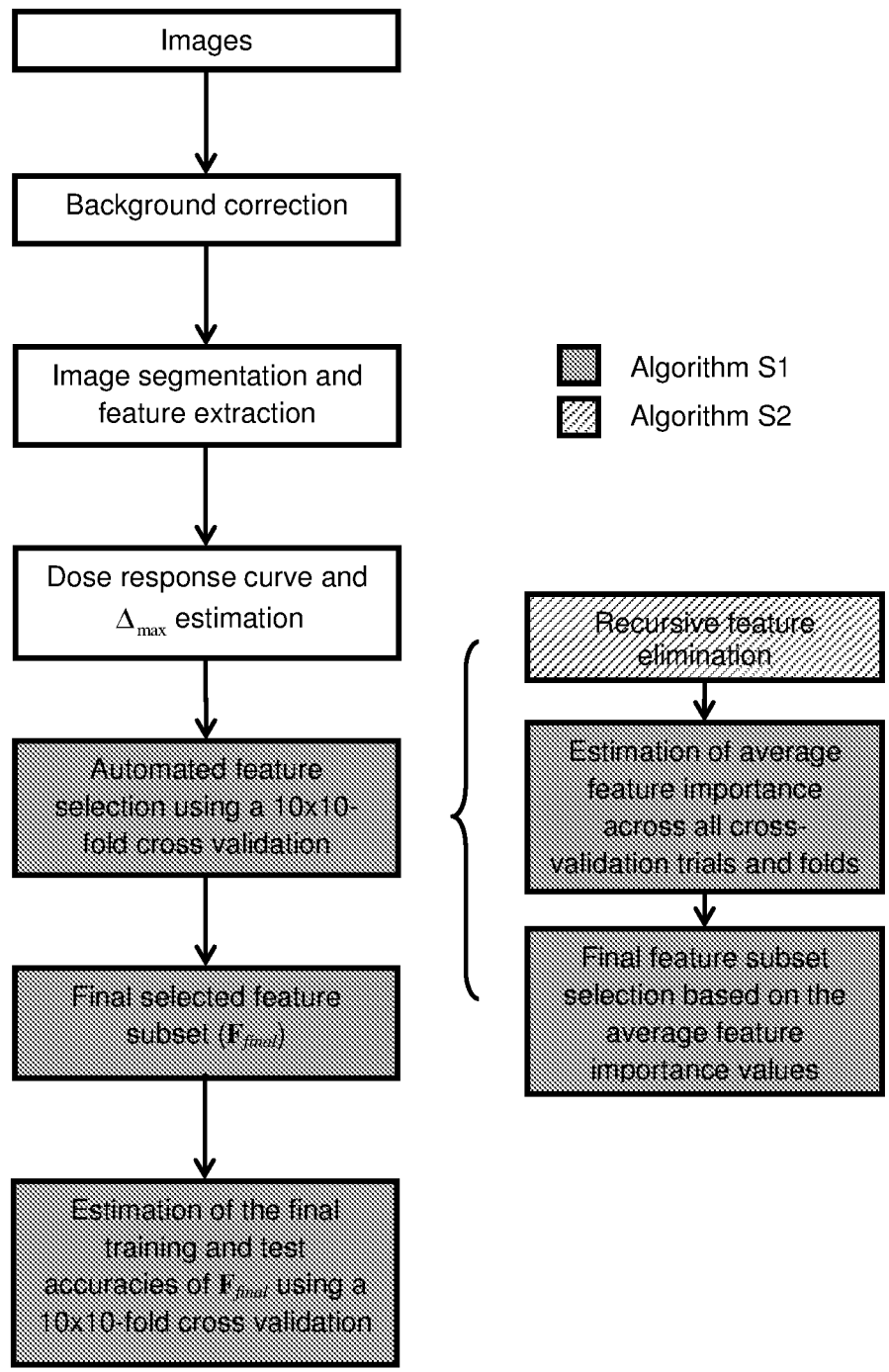
FIG. 2 depicts a flowchart of an imaging and data analysis method used by the computing device of the system of FIG. 1 for high throughput in vitro modelling for accurate prediction of compound-induced liver injury in accordance with the present embodiment.

Referring to FIG. 2, a flowchart 200 depicts an imaging and data analysis method used by the computing device 130 for high throughput prediction of compound-induced hepatocyte injury in vivo in accordance with the present embodiment. The computing device 130 receives the images 202 and performs background correction 204 to improve the clarity of the image in preparation for image segmentation and feature extraction 206 by the feature extraction module 132. The prediction module performs a dose response curve fitting and $\Delta_{max}$ estimation process 208 before performing an automated feature selection 210 on the processed image.

The automated feature selection 210 in accordance with the present embodiment includes two novel methods: a recursive feature elimination algorithm 212 and a feature selection algorithm. The feature selection algorithm is performed after the recursive feature elimination algorithm 212 and includes a feature importance estimation step 214 and a final feature subset selection step 216. The feature importance estimation step 214 includes estimation of average feature importance across all 10×10-fold cross validation trials and folds. And the final feature subset selection step 216 includes final feature subset selection based on average feature importance values obtained at step 214.

The result is a final selected feature subset $F_{final}$ 218. For validation, an estimation of the final training and test accuracies of $F_{final}$ is performed using 10×10-fold cross validation 220.

Referring to FIG. 3, comprising FIGS. 3A to 3F, images 300, 310, 320, 330, 340, 350 depict exemplary immunofluorescence image data obtained with different compounds after fluorescent staining of RELA (red) and nuclear DNA (blue) in accordance with the present embodiment. Referring to FIG. 3A, the image 300 depicts fluorescently stained HepaRG cells obtained from a cell culture in which the cells have been treated with 100 μg/mL puromycin (positive control). Referring to FIGS. 3B and 3C (images 310, 320) the cells have been treated with 1000 μg/mL acarbose 1000 μg/mL tetracycline, respectively. Both compounds are toxic for hepatocytes in vivo.

Referring to FIG. 3D, the image 330 depicts fluorescently stained cells of the vehicle control. And referring to FIGS. 3E and 3F, (images 340 and 350) the cells have been treated with 100 μg/mL ethylene glycol and 1000 μg/mL lithium chloride, respectively.

The images 300, 310, 320, 330, 340, 350 depict HepaRG cells imaged by high-throughput screening with a high content analyzer (imaging device 120). Hepatotoxicants in the images 300, 310, 320 induced phenotypic changes and an altered distribution of RELA (NF-κB p65) 302 in comparison to the vehicle control image 330. Such phenotypic changes were not observed when cells were treated with non-hepatotoxic compounds as shown in the images 340, 350. The hepatotoxicant acarbose (the image 310) is not toxic for the human renal proximal tubular cells. Thus, in previous studies on renal models, changes of human primary renal proximal tubular cells (HPTC) or HPTC-like cells induced by the hepatotoxicant acarbose were not observed; however, the hepatotoxicant acarbose induced obvious changes in HepaRG cells as shown in the image 310. Ethylene glycol (nephrotoxic and neurotoxic) and lithium chloride (nephrotoxic) are both toxic in humans for other organs than the liver. Yet, these compounds did not induce obvious phenotypic changes in HepaRG cells as shown in the images 340, 350. These and other results suggest that the responses of the cells are highly organ-specific. In conventional hepatotoxicity testing, almost all non-hepatotoxic compounds with other toxicities in humans gave positive results with HepG2-based models. Therefore, in contrast to the HepaRG-based model in accordance with the present embodiment, the conventional HepG2-based models are not liver-specific, but detect cytotoxicity in general.

Referring to FIG. 4 a table of reference compound information used for validation of the high-throughput method in accordance with the present embodiment for accurate prediction of compound-induced injury is depicted. Those compounds that have been identified as toxic for hepatocytes in humans based on a literature survey using PubMed™ and Google® are indicated by "+".

Referring to FIG. 5, the table shows the final selected feature subset $F_{final}$ (218) consisting of 4 features. $\Delta_{max}$ (208) is indicated with respect to the estimated final training and test accuracies (220). The results were obtained with fluorescently labelled HepaRG cells and the set of 98 compounds (FIG. 4) used for pre-validation.

FIG. 6 depicts a table of reference compound information used for pre-validation of the high-throughput method with induced pluripotent stem cell (iPS)-derived hepatocyte-like cells in accordance with the present embodiment for accurate prediction of compound-induced injury.

Figure 7:
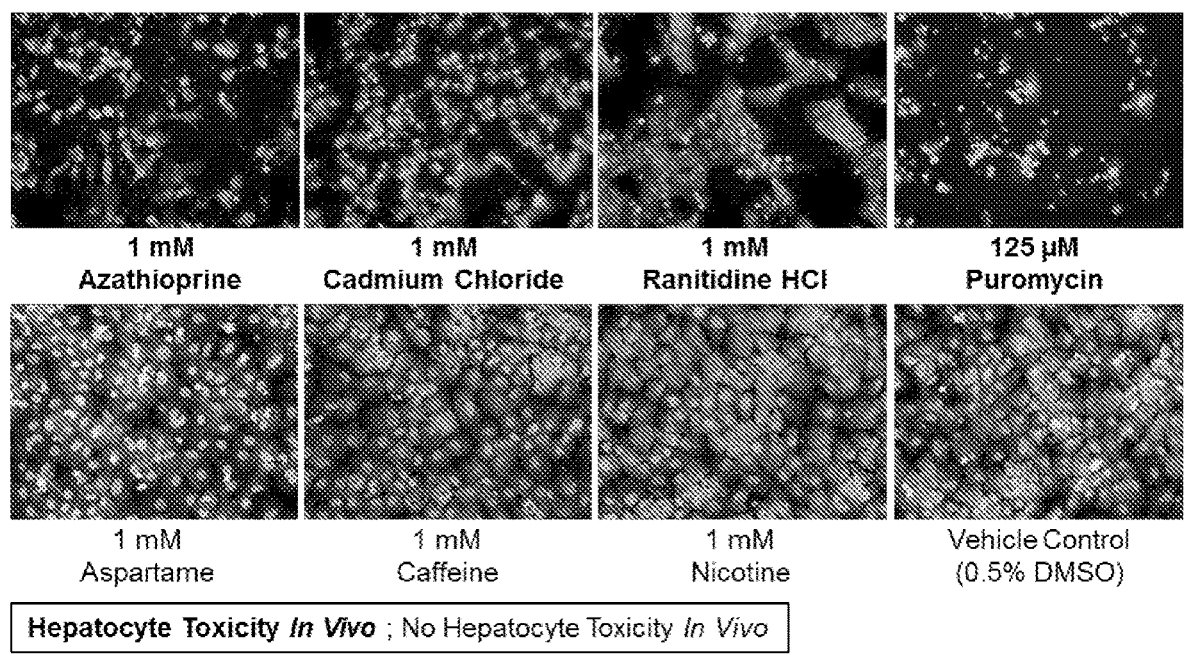
FIG. 7 shows image data illustrating phenotypic changes of iPS-derived hepatocyte-like cells induced by compounds that injure hepatocytes in vivo.

FIG. 7 shows image data illustrating phenotypic changes of iPS-derived hepatocyte-like cells induced by compounds that injure hepatocytes in vivo. In particular, in FIG. 7, iPS-derived hepatocyte-like cells (iCell Hepatocytes) were treated with compounds at the indicated concentrations that are known to be toxic (compounds listed in top row—Azathioprine, Cadmium Chloride, Ranitidine HCL, Puromycin) or not toxic (compounds listed in bottom row—Aspartame, Caffeine, Nicotine, DMSO) for hepatocytes in vivo (classification based on literature on compound-induced clinical effects in humans) and respective positive (125 μM puromycin) and vehicle (0.5% dimethyl-sulfoxide, DMSO) controls. The cells were imaged by high content screening after immunofluorescent staining of RELA (red) and nuclear DNA (blue). These image data show examples phenotypic cellular changes that were induced by compounds that damage hepatocytes in vivo (images at the top row).

iCell Hepatocytes (iCells) were purchased from Cellular Dynamics (Madison, Winconsin, USA). iCells were thawed with RPMI medium containing 1×B27, 20 ng/mL Oncostatin M, 0.1 μM Dexamethasone, 25 μg/mL Gentamicin and 1× iCell Hepatocyte Medium Supplement.

iCells were then seeded into collagen I coated 384-well plates at a seeding density of 30,000 cells per well. The cells were cultivated for 7 days before compound treatment. iCells were treated for 16 hours with test compounds at a dose-range of 7 concentrations which ranged from 2 μM to 1 mM.

The library used for pre-validation contained 24 compounds with well-documented clinical effects on hepatocytes in humans (subset of the 98 compounds listed in FIG. 4). The library contained diverse types of chemicals including drugs, industrial chemicals, agrochemicals, environmental toxicants and food additives.

After compound treatment, biomarkers were detected by immunostaining and the whole cells were stained with WCS. High-content screening was performed with a 20× objective using the ImageXpress Micro XLS system (Molecular Devices, Sunnyvale, Calif., USA).

Example

To demonstrate the present embodiment, HepG2 cells (used as controls) and HepaRG cells were purchased from the American Type Culture Collection (ATCC. Manassas. Va., USA) and ThermoFisher Scientific (Singapore), respectively. The HepG2 cells were cultured in T75 Corning Costar flasks with Dulbecco's modified eagle medium (DMEM) supplemented with 10% fetal bovine serum (FBS) and 1% penicillin-streptomycin. The HepG2 cells were seeded into 384-well black plates with transparent bottom (#781091; Greiner, Kremsmuenster, Austria) at a density of 10.000 cells/cm². The HepG2 cells were cultured for three days to attain confluency before overnight compound treatment of sixteen hours. The HepaRG cells were directly seeded at a density of 250.000 cells/cm² into 384-well black plates with transparent bottom (#781091; Greiner) coated with 100 μg/mL collagen I. For the first twenty-four hours of cultivation a Williams E medium, supplemented with HepaRG Thaw, Plate & General Purpose medium was used. Subsequently, the HepaRG cells were cultivated for seven days in Williams E medium supplemented with HepaRG Tox medium and 1% GlutaMAX (all media and supplements from ThermoFisher Scientific) with medium replenishment on day 1 and day 4 of the culture. The HepaRG cells were cultured for 7 days before overnight compound treatment of 16 hours. The protocol of HepaRG culture for toxicity studies was obtained from ThermoFisher Scientific.

Compound Treatment

The cells were treated for sixteen hours with 98 compounds as listed in the table of FIG. 4. Screening was performed by using a dose-range of the following seven concentrations for each compound: 2 μM, 15 μM, 63 μM, 125 μM, 250 μM, 500 μM and 1 mM. Puromycin (125 μM) and chlorpromazine (15 μM) were used as positive controls, while dexamethasone (250 μM and 1 mM) was used as a negative control. Untreated cells (no drug, no vehicle) and respective vehicle controls (dimethyl sulfoxide (DMSO) or water) were included in every plate. Four technical replicates were included for each treatment condition (four wells per data point). Z' values of each plate were calculated and values were all above 0.5, ranging from 0.62 to 0.89.

Immunostaining

Cells were fixed for six hours with 3.7% formaldehyde in phosphate-buffered saline (PBS) after sixteen hours of compound exposure. Cells were then blocked and permeabilized with PBS containing 5% bovine serum albumin (BSA) and 0.2% Triton X-100 for one hour at room temperature. Subsequently, samples were incubated for one hour at room temperature with either a rabbit polyclonal anti-RELA antibody (#ab16502; Abcam, Cambridge, UK) at 1 μg/mL or a mouse monoclonal anti-gamma H2AX (phosphor S139) antibody (#ab26350; Abcam) at 2 μg/mL. Samples were then incubated with either a goat anti-rabbit secondary antibody conjugated with Alexa-488 (#A11008; Life Technologies, Singapore) or a goat anti-mouse secondary antibody conjugated with Alexa-647 (#A21235, Life Technologies) at 5 μg/mL. F-actin was detected on every plate with rhodamine phalloidin (#R415; 1:100; Invitrogen, Singapore). Cell nuclei and whole cells were stained on every plate with 4', 6-diamidino-2phenylindole dihydrochloride (DAPI; #268298; Merck, Darmstadt, Germany) at 4 ng/mL, and whole cell stain red (WCS; #8403402; 1:100; Cellomics, Rockford, United States of America).

Image Acquisition

Automated imaging was performed with a 20× objective with the ImageXpress$^{MICRO}$ system (Molecular Devices, Sunnyvale, Calif., USA). Nine sites per well were imaged with four channels and the images were saved in a 16-bit TIFF format.

Image Segmentation and Feature Extraction

To reduce non-uniform background illuminations, the images were corrected using the "rolling ball" algorithm implemented in ImageJ (NIH, v1.48). Cell segmentations and feature measurements were performed using a cellXpress™ proprietary software platform.

Haralick's Texture Features

A grey-level co-occurrence matrix (GLCM) is a matrix that describes the distribution of co-occurring grey-level values at a given offset $(\Delta x, \Delta y)$ in an $N_x \times N_y$ image, $I(x, y)$, with $N_g$ grey levels. In these notations, x and y are the row and column indices, respectively. The GLCM matrix is defined by Equation 1.

$$GLCM_{\Delta x, \Delta y}(i, j) = \sum_{x=1}^{N_x} \sum_{y=1}^{N_y} \begin{cases} 1, & \text{if } I(x, y) \text{ and } I(x+\Delta x, y+\Delta y) = j \\ 0, & \text{otherwise} \end{cases} \quad (1)$$

where i and j are the grey-level or intensity values of the image. The normalized GLCM matrix is $$p(i, j, \Delta x, \Delta y) = \frac{GLCM_{\Delta x, \Delta y}(i, j)}{\sum_{i=1}^{N_g} \sum_{j=1}^{N_g} GLCM_{\Delta x, \Delta y}(i, j)} \quad (2)$$

The sum probability matrix is calculated to be $$p_{x+y}(k, \Delta x, \Delta y) = \Sigma N_{x=1}^{N_g} \Sigma_{y=1}^{N_g} p(i, j, \Delta x, \Delta y) \quad (3)$$

where k=2, 3, _, $2N_g$. The sum average of GLCM are shown in Equations (4).

$$f_{SA}(\Delta x, \Delta y) = \Sigma_{k=2}^{2N_g} k p_{x+y}(k, \Delta x, \Delta y) \quad (4)$$

In the validation study, the images were the bounding boxes around the segmented cells with all the background pixels set to zero. The images were then quantized into $N_g=256$ grey levels, and all the Haralick's features for 0 degree ($\Delta x=0, \Delta y=1$), 45 degree ($\Delta x=1, \Delta y=1$), 90 degree ($\Delta x=1, \Delta y=0$), and 135 degree ($\Delta x=1, \Delta y=-1$) offsets were computed. For each feature, the mean of all the offset values was used and the cellXpress™ software platform was used to extract all the texture features.

Concentration Response Curve and $\Delta_{max}$ Estimations

After feature extraction, the values of a feature were divided at all the tested compound concentrations by the values of the feature under the corresponding vehicle control conditions. Then, the ratios were log 2-transformed ($\Delta$). All further data analyses, including building concentration response curves and toxicity classifiers, were performed using customized scripts under the R statistical environment (the R foundation, v3.0.2) and the Windows 7 operating system (Microsoft, USA).

For each feature, the concentration response curve was estimated using a standard log-logistic model as shown in Equation (5).

$$\Delta(x, (b, c, d, e)) = \frac{d - c}{1 + \exp\{b(\log(x) - \log(e))\}} \quad (5)$$

where x is the xenobiotics compound concentration, e is the response half-way between the lower limit c and upper limit d, and b is the relative slope around e. The "drc" library (v 2.3-96) under the R environment was used to fit the values of b, c, d, and e. After that, the maximum response values ($\Delta_{max}$) were determined using the estimated response curves. In theory, $\Delta_{max}$ should be equal to the upper limit d. However, in practice, the responses of some compounds may not plateau even at the highest tested dosages. Therefore the estimated d value may not be accurate. Instead, $\Delta_{max}$ was fixed to be the response value at either 1, 2, or 5 mM, which was around the highest tested concentrations for most of the compounds. Finally, the median values of $\Delta_{max}$ across all the replicates were computed.

Feature Normalization

Before data classification, each feature vector $f_i$ was normalized to the same range [−1, 1] as shown in Equation (6).

$$f_i \leftarrow 2 \frac{(f_i - f_{min})}{f_{max} - f_{min}} - 1 \quad (6)$$

where $f_{min}$ and $f_{max}$ are the minimum and maximum values of the feature. To ensure the training and test datasets were independent from each other, these two normalization coefficients were estimated only using the training data, but were applied to both the training and the test datasets.

Random Forest Classification

A random-forest algorithm was used to predict xenobiotic-induced nephrotoxicity, as this algorithm has previously been shown to outperform other commonly-used classifiers, including support vector machines, k-nearest neighbors and naïve Bayes. In addition, the "randomForest" library (v4.6-10) under the R environment was used.

Classification Performance Estimation

A stratified 10-fold cross validation procedure was used to estimate the toxicity prediction performance of the phenotypic features. The performance measurements used are shown in Equations (7), (8) and (9).

$$\text{Sensitivity} = \frac{TP}{TP + FN} \times 100\% \quad (7)$$

$$\text{Specificity} = \frac{TN}{TN + FP} \times 100\% \quad (8)$$

$$\text{Balanced Accuracy } (acc) = \frac{\text{Sensitivity} + \text{Specificity}}{2} \quad (9)$$

where TP is the number of true positives, TN is the number of true negatives, FP is the number of false positives and FN is the number of false negatives. FIG. 5 depicts a table summarizing the overall prediction performance for single- and multi-feature classifiers for all three datasets in accordance with the present embodiment.

Referring to FIG. 5, a table lists the phenotypic feature sets and their prediction performance with HepaRG cells when tested against the ninety-eight compounds listed in FIG. 4 in accordance with present embodiment. The phenotypic feature sets include: a coefficient of variation of the intensity of a DNA marker at the chromosomal region, an average of the sum average of the DNA grey-level co-occurrence matrix (GLCM) at the nuclear region, an average of the intensity of a RELA marker at the chromosomal region, and a fraction of the total intensity of the RELA objects at the nuclear region. Nuclear fraction of the RELA $$\text{objects} = \frac{I(C \cap D)}{I(D)},$$

where RELA objects are the subcellular regions that have high levels of RELA stains, I(D) is the sum of the intensity values of all the pixels at the RELA-object regions, and I(C∩D) is the sum of the intensity values of all the pixels at the intersection of the cytoplasmic and RELA-object regions. Using a concentration of 1 mM to estimate the maximum response values ($\Delta_{max}$) of the combination of these feature sets resulted in a test sensitivity of 47.9-61.4%, a test specificity of 86.1-92.1% and a test accuracy of 70.0-73.8%.

Thus it can be seen that the present embodiment provides an improved predictive model for drug-induced liver injury in humans utilizing an accurate and high-throughput screening (HTS)-based method and system for predicting compound-induced hepatocyte injury in vivo. Predicting hepatocyte toxicity in vivo in accordance with the present embodiment is based on HepaRG cells and not on HepG2 cells and high sensitivity and accuracy has been achieved (for the 98 compounds tested, test sensitivity is 61.4%, test specificity is 86.1%, and test balanced accuracy is 73.8%).

Unlike conventional models which determine the toxicity of compounds for cultivated hepatocytes, the system and methods in accordance with the present embodiment only look at changes induced in in vitro cultivated cells and use these changes to predict hepatocyte toxicity in vivo. The HTS model in accordance with the present embodiment makes binary predictions and gives a yes/no answer with respect to hepatocyte toxicity in vivo. No predictions however can be made with respect to the dose. This can be overcome by complementing the HTS model with computational models or other in vitro models that predict the human dose response. Such models are still at the experimental stage, but in the future this may be an option. An advantage of the present embodiment is its high throughput. It can be efficiently applied at very early stages of compound screening and would allow the flagging of all compounds that are predicted to be toxic for hepatocytes in vivo. For most of these compounds, more detailed information on the dose response might not be required.

Further, the disclosure comprises embodiments according to the following clauses:

Clause 1. A method for predicting human liver injury induced by a test compound comprising: acquiring images of fluorescently stained cells obtained from a cell culture in which the cells have been treated with a dose-range of at least the test compound and its vehicle; segmenting the acquired images; extracting and analyzing one or more phenotypic features from the segmented images, wherein the one or more phenotypic features are selected from the group of intensity, textural, morphological, or ratiometric features consisting of (a) features of DNA, (b) features of a RELA (NF-κB p65), and (c) features of actin filaments at different subcellular regions in the segmented images; normalizing results from the treated samples to vehicle controls; and predicting a probability of human liver injury by the test compound based on test compound-induced normalized phenotypic changes of the extracted phenotypic features using a supervised classifier.

Clause 2. The method in accordance with Clause 1, wherein extracting the one or more phenotypic features from the segmented images comprises extracting the phenotypic feature measuring a coefficient of variation of DNA intensity at chromosomal regions in the segmented images.

Clause 3. The method in accordance with Clause 1, wherein extracting the one or more phenotypic features from the segmented images comprises extracting two phenotypic features consisting of (a) a fraction of a total DNA object intensity at chromosomal regions in the segmented images and (b) an average of a sum of a variance of a RELA marker determined from a grey-level co-occurrence matrix (GLCM) at nuclear regions in the segmented images.

Clause 4. The method in accordance with Clause 1, wherein extracting the one or more phenotypic features from the segmented images comprises extracting four phenotypic features consisting of (a) a fraction of a total DNA object intensity at chromosomal regions in the segmented images, (b) an average of a sum of a variance of a RELA determined from a grey-level co-occurrence matrix (GLCM) at nuclear regions in the segmented images, (c) a perimeter of one or more of the nuclear regions in the segmented images, and (d) ratios of total RELA intensity between the chromosomal regions and the nuclear regions in the segmented images.

Clause 5. The method in accordance with Clause 1, wherein the cells are selected from the group comprising differentiated hepatic cells, induced pluripotent stem cell (iPS)-derived human hepatocyte-like cells, primary human hepatocytes, and an (immortalized) human hepatocyte cell line.

Clause 6. The method in accordance with Clause 5, wherein the differentiated hepatic cells are derived from a human hepatic progenitor-like cell line.

Clause 7. The method in accordance with Clause 6, wherein the differentiated hepatic cells derived from a human hepatic progenitor-like cell line are HepaRG™ cells.

Clause 8. The method in accordance with any one of Clauses 1 to 7 wherein the cells of the cell culture are cultured in a 2D culture.

Clause 9. The method in accordance with any one of Clauses 1 to 8 further comprising the step of fluorescently labelling the cells cultured in the cell culture for detection of one or more of DNA, RELA (NF-κB p65), F-actin, gammaH2AX and a whole cell.

Clause 10. The method in accordance with any one of Clauses 1 to 9 wherein treating the cells comprises treating human hepatocytes with the at least one test compound and the vehicle for a predetermined time duration of at least twelve hours or overnight.

Clause 11. The method in accordance with Clause 10 wherein treating the cells comprises treating human hepatocytes with the at least one test compound and the vehicle for a predetermined time duration of sixteen hours or greater.

Clause 12. The method in accordance with any one of Clauses 1 to 11 wherein predicting human hepatotoxicity comprises: treating the cells with a dose-range of at least one test compound and the vehicle; determining maximal response values ($\Delta_{max}$) with respect to the phenotypic features; and using the supervised classifier to predict human hepatotoxicity based on the compound-induced feature changes.

Clause 13. The method in accordance with Clause 12 wherein using the supervised classifier to predict human hepatotoxicity comprises using the supervised classifier that uses a median of the maximal response values ($\Delta_{max}$) of the normalized phenotypic feature changes of the cells for compound classification.

Clause 14. The method in accordance with Clause 12, when the maximal response values comprise response values at a concentration of 1 mM, 2 mM or 5 mM of the test compound.

Clause 15. The method in accordance with Clause 1 wherein predicting liver toxicity in humans comprises: normalizing the phenotypic features from different test compounds to a same range when more than one test compound is tested; and predicting liver toxicity in humans by using a machine learning classification algorithm that has been trained with a training set of compounds that is statistically independent from a test set of compounds.

Clause 16. The Clause in accordance with Clause 15, wherein the machine learning classification algorithm is a random-forest algorithm.

Clause 17. The method in accordance with Clause 15, wherein the machine learning classification algorithm is a support vector machine.

Clause 18. A system for predicting human liver injury induced by at least one test compound comprising: an apparatus for treating a cell culture with the at least one test compound and its vehicle and staining the cell culture for fluorescent detection; an imaging device arranged with respect to the apparatus to acquire images of the fluorescently stained cells for detecting the cells and their stained components; and a computing device coupled to the imaging device for receiving and segmenting the acquired images, the computing device comprising a feature extraction module for extracting and analyzing one or more phenotypic features from the segmented images, wherein the one or more phenotypic features are selected from the group of intensity, textural, morphological, or ratiometric features consisting of (a) features of DNA, (b) features of a RELA (NF-κB p65), and (c) features of actin filaments at different subcellular regions in the segmented images, the computing device further comprising a prediction module for normalizing results from the treated samples to vehicle controls and predicting a probability of human liver injury by the test compound based on test compound-induced normalized phenotypic changes of the extracted phenotypic features using a supervised classifier.

Clause 19. The system in accordance with Clause 18 wherein the feature extraction module extracts a phenotypic feature from the segmented images measuring a coefficient of variation of DNA intensity at chromosomal regions in the segmented images.

Clause 20. The system in accordance with Clause 19 wherein the feature extraction module extracts two phenotypic features consisting of (a) a fraction of a total DNA object intensity at chromosomal regions in the segmented images and (b) an average of a sum of a variance of a RelA marker determined from a grey-level co-occurrence matrix (GLCM) at nuclear regions in the segmented images.

Clause 21. The system in accordance with Clause 19 wherein the feature extraction module extracts four phenotypic features consisting of (a) a fraction of a total DNA object intensity at chromosomal regions in the segmented images, (b) an average of a sum of a variance of a RelA marker determined from a grey-level co-occurrence matrix (GLCM) at nuclear regions in the segmented images, (c) a perimeter of one or more of the nuclear regions in the segmented images, and (d) ratios of total RelA marker intensity between the chromosomal regions and the nuclear regions in the segmented images.

Clause 22. The system in accordance with any of Clauses 19 to 21 wherein the prediction module of the computing device predicts human hepatotoxicity by using a supervised classifier based on maximum response values ($\Delta_{max}$) with respect to the phenotypic feature changes of the cells treated with the at least one test compound and the vehicle.

Clause 23. The system in accordance with Clause 22 wherein the prediction module of the computing device predicts human hepatotoxicity by using a supervised classifier that uses a median of the maximum response values ($\Delta_{max}$) of the normalized phenotypic feature changes.

Clause 24. The system in accordance with Clause 22, wherein the maximum response values comprises response values at a compound concentration of 1 mM, 2 mM or 5 Mm of the test compound.

Clause 25. The system in accordance with any one of Clauses 20 to 24 wherein the prediction module of the computing device predicts human hepatotoxicity based on changes of phenotypic features normalized to a same range when more than one test compound is used and by using a machine learning classification algorithm trained with a statistically independent training set of compounds.

Clause 26. The system in accordance with Clause 25 wherein the machine learning classification algorithm is a random forest algorithm.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. A method for predicting liver injury induced by a test compound comprising:
    acquiring images of fluorescently stained cells obtained from a cell culture in which the cells have been treated with a dose-range of at least the test compound and its vehicle;
    segmenting the acquired images;
    extracting and analyzing, one or more phenotypic features from the segmented images, wherein the one or more phenotypic features are features of (a) DNA, (b) a RELA (NF-κB p65), and (c) cellular organdies and their substructures in the segmented images selected from the group of intensity, textural, morphological, or ratiometric features;
    normalizing results from the treated samples to vehicle controls; and
    predicting a probability of liver injury by the test compound based on test compound-induced normalized changes of the extracted and selected phenotypic features using machine learning methods,
    wherein extracting and selecting the one or more phenotypic features from the segmented images comprises extracting and selecting one or more of (i) an average of the intensities and/or their ratios of a RELA marker at nuclear and/or cellular regions in the segmented images, and/or (ii) a fraction of the intensity of objects based on a RELA marker at nuclear and other cellular regions in the segmented images, and/or (iii) the ratio of the intensities of an actin and a RELA marker at cellular regions, and/or (iv) the correlation between DNA and RELA intensities at subcellular regions.

2. The method in accordance with claim 1, wherein extracting and selecting the one or more phenotypic features from the segmented images further comprises extracting and selecting an average of a sum average of the intensity of a DNA marker determined from a grey-level co-occurrence matrix (GLCM) at nuclear regions in the segmented images.

3. The method in accordance with claim 1, wherein the cells are selected from the group comprising hepatic cells, induced pluripotent stem cell (iPS)-derived hepatocyte-like cells, primary hepatocytes, an (immortalized) hepatocyte cell line, and hepatoma cells.

4. The method in accordance with claim 3, wherein the hepatic cells are derived from hepatic progenitor-like cells.

5. The method in accordance with claim 3, wherein the cells are one of human cells or animal cells.

6. The method in accordance with claim 1 wherein the cells of the cell culture are cultured in a 2D culture.

7. The method in accordance with claim 1 further comprising the operation of fluorescently labelling the cells for detection of RELA (NF-κB p65) and one or more of DNA, F-actin, gammaH2AX and the whole cells.

8. The method in accordance with claim 1 wherein treating the cells comprises treating with the at least one test compound and the vehicle for a predetermined time duration of at least twelve hours or overnight.

9. The method in accordance with claim 8 wherein treating the cells comprises treating with the at least one test compound and the vehicle for a predetermined time duration of sixteen hours or greater.

10. A method for predicting liver injury induced by a test compound comprising:
    acquiring images of fluorescently stained cells obtained from a cell culture in which the cells have been treated with a dose-range of at least the test compound and its vehicle;
    segmenting the acquired images;
    extracting and analyzing one or more phenotypic features from the segmented images, wherein the one or more phenotypic features are features of (a) DNA, (b) a RELA (NF-κB p65) and (c) cellular organelles and their substructures in the segmented images selected from the group of intensity, textural, morphological, or ratiometric features;
    normalizing results from the treated samples to vehicle controls; and
    predicting a probability of liver injury by the test compound based on test compound-induced normalized changes of the extracted and selected phenotypic features using machine learning methods, wherein predicting the probability of liver injury by the test compound comprises:
        treating the cells with a dose-range of the test compound and the vehicle;
        determining maximal response values ($\Delta_{max}$) with respect to the phenotypic features; and using machine learning methods to predict hepatotoxicity based on the maximal response values ($\Delta_{max}$) of the compound-induced feature changes, wherein extracting and selecting the one or more phenotypic features from the segmented images comprises extracting and selecting one or more of (i) an average of the intensities and/or their ratios of a RELA marker at nuclear and/or cellular regions in the segmented images, and/or (ii) a fraction of the intensity of objects based on a RELA marker at nuclear and other cellular regions in the segmented images, and/or (iii) the ratio of the intensities of an actin and a RELA marker at cellular regions, and/or (iv) the correlation between DNA and RELA intensities at subcellular regions.

11. The method in accordance with claim 10 wherein using machine learning methods to predict hepatotoxicity comprises using machine learning methods that use a median of the maximal response values ($\Delta_{max}$) of the selected and normalized phenotypic feature changes of the cells for compound classification.

12. The method in accordance with claim 10, when the maximal response values comprise response values at a concentration of 1 mM, 2 mM or 5 mM of the test compound.

13. The method in accordance with claim 10 wherein predicting the probability of liver injury comprises:

normalizing the phenotypic features from different test compounds to a same range when more than one test compound is tested; and predicting the probability of liver injury by using a machine learning classification algorithm that has been trained with a training set of compounds that is statistically independent from a test set of compounds.

14. The method in accordance with claim 13, wherein the machine learning classification algorithm comprises one of a random-forest algorithm or a support vector machine.

15. A system for predicting liver injury induced by at least one test compound comprising:

an apparatus for treating a cell culture with the at least one test compound and its vehicle and staining the cell culture for fluorescent detection;

an imaging device arranged with respect to the apparatus to acquire images of the fluorescently stained cells for detecting the cells and their stained components; and a computing device coupled to the imaging device for receiving and segmenting the acquired images, the computing device comprising a feature extraction module for extracting and analyzing one or more phenotypic features from the segmented images, wherein the one or more phenotypic features are features of (a) DNA, (b) a RELA (NF-κB p65), and (c) cellular organelles and their substructures in the segmented images selected from the group of intensity, textural, morphological, or ratiometric features, the computing device further comprising a prediction module for normalizing results from the treated samples to vehicle controls and predicting a probability of liver injury by the test compound based can test compound-induced normalized changes of the extracted and selected phenotypic features using machine learning methods, wherein the feature extraction module extracts and selects a phenotypic feature from the segmented images for analysis by measuring one or more of (i) an average of the intensities and/or their ratios of a RELA marker at nuclear and/or cellular regions in the segmented images, and/or (ii) a fraction of the intensity of objects based on a RELA marker at nuclear and other cellular regions in the segmented images, and/or (iii) the ratio of the intensities of an actin and a RELA marker at cellular regions, and/or (iv) the correlation between DNA and RELA intensities at subcellular regions.

16. The system in accordance with claim 15 wherein the feature extraction module extracts and selects a phenotypic feature from the segmented images measuring an average of a sum average of the intensity of a DNA marker determined from a grey-level co-occurrence matrix (LLCM) at nuclear regions in the segmented images.

17. The system in accordance with claim 15 wherein the prediction module of the computing device predicts hepatotoxicity by using machine learning methods based on maximum response values ($\Delta_{max}$) with respect to the phenotypic feature changes of the cells treated with the at least one test compound and the vehicle.

18. The system in accordance with claim 17 wherein the prediction module of the computing device predicts hepatotoxicity by using machine learning methods that uses a median of the maximum response values ($\Delta_{max}$) of the selected and normalized phenotypic feature changes.

19. The system in accordance with claim 17, wherein the maximum response values comprises response values at a compound concentration of 1 mM, 2 mM or 5 mM of the test compound.

20. The system in accordance with claim 15 wherein the prediction module of the computing device predicts hepatotoxicity based on changes of phenotypic features normalized to a same range when more than one test compound is used and by using a machine learning classification algorithm trained with a statistically independent training set of compounds, and wherein the machine learning classification algorithm comprises one of either a random forest algorithm or a support vector machine.

* * * * *